(12) United States Patent
Yen et al.

(10) Patent No.: US 11,475,633 B2
(45) Date of Patent: Oct. 18, 2022

(54) METHOD AND SYSTEM FOR 3D IMAGE DYNAMIC CORRECTION EVALUATION AND ORTHOTICS AUXILIARY DESIGN

(71) Applicant: INDUSTRIAL TECHNOLOGY RESEARCH INSTITUTE, Hsinchu (TW)

(72) Inventors: Po-Fu Yen, New Taipei (TW); Zhong-Yi Haung, Fenyuan Township (TW); Shang-Yi Lin, Taichung (TW); Tian-Li Yu, Taipei (TW); Tzong-Ming Wu, Taipei (TW); Tsung-Wen Tsai, New Taipei (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 23 days.

(21) Appl. No.: 17/308,413

(22) Filed: May 5, 2021

(65) Prior Publication Data

US 2022/0180606 A1 Jun. 9, 2022

(30) Foreign Application Priority Data

Dec. 3, 2020 (TW) ................................. 109142659

(51) Int. Cl.
*G06T 17/00* (2006.01)
*G06T 17/20* (2006.01)
(Continued)

(52) U.S. Cl.
CPC ............ *G06T 17/205* (2013.01); *G06F 30/23* (2020.01); *G06N 7/005* (2013.01); *G06T 19/20* (2013.01);
(Continued)

(58) Field of Classification Search
None
See application file for complete search history.

(56) References Cited

U.S. PATENT DOCUMENTS

2008/0091171 A1 4/2008 Strommer et al.
2014/0169647 A1 6/2014 Ruszczycki et al.
(Continued)

FOREIGN PATENT DOCUMENTS

CN 103959333 A 7/2014
CN 106214302 A 12/2016
(Continued)

OTHER PUBLICATIONS

Clin et al., "Comparison of the biomechanical 3D efficiency of different brace designs for the treatment of scoliosis using a finite element model," Eur. Spine J., vol. 19, 2010, pp. 1169-1178.
(Continued)

*Primary Examiner* — Martin Mushambo
(74) *Attorney, Agent, or Firm* — Birch, Stewart, Kolasch & Birch, LLP

(57) ABSTRACT

A three-dimensional (3D) image dynamic correction evaluation and auxiliary design method for orthotics includes the following steps. 3D scanning information of the human body is obtained. A plurality of 2D images of the human body is obtained for identification, and the pixel values of the 2D images are calculated so as to synthesize an original 3D spine curve. The 2D images of the human body and the 3D scan information are synthesized. An image deformation prediction and correction method of body shape is used to generate a deformed body shape of the human body. A spine material properties and mechanical model prediction method is used to predict parameters of the position, direction and magnitude of the force applied by an orthotics to the human body according to the deformed body shape.

16 Claims, 11 Drawing Sheets

(51) Int. Cl.
  *G06T 19/20* (2011.01)
  *G06F 30/23* (2020.01)
  *G06N 7/00* (2006.01)

(52) U.S. Cl.
  CPC .. *G06T 2210/41* (2013.01); *G06T 2219/2004* (2013.01); *G06T 2219/2016* (2013.01)

(56) References Cited

U.S. PATENT DOCUMENTS

| | | | |
|---|---|---|---|
| 2014/0330187 A1 | 11/2014 | Perez et al. | |
| 2015/0313566 A1 | 11/2015 | Diers et al. | |
| 2017/0143426 A1* | 5/2017 | Isaacs | A61B 34/20 |

FOREIGN PATENT DOCUMENTS

| | | |
|---|---|---|
| CN | 110327146 A | 10/2019 |
| CN | 110634554 A | 12/2019 |
| CN | 111311742 A | 6/2020 |
| TW | M443156 U1 | 12/2012 |
| TW | 201818892 A | 6/2018 |
| TW | 201926253 A | 7/2019 |
| TW | 202008163 A | 2/2020 |
| WO | WO 2019/014452 A1 | 1/2019 |

OTHER PUBLICATIONS

Fortin et al., "A 3D visualization tool for the design and customization of spinal braces," Computerized Medical Imaging and Graphics, vol. 31, 2007, pp. 614-624.

Sattout et al., "Biomechanical Assessment of Providence Nighttime Brace for the Treatment of Adolescent Idiopathic Scoliosis," Spine Deformity, vol. 4, 2016, pp. 253-260.

Van Den Hout et al., "Interface corrective force measurements in Boston brace treatment," Eur. Spine J., vol. 11, 2002, pp. 332-335.

Weinstein et al., "Design of the Bracing in Adolescent Idiopathic Scoliosis Trial (BrAIST)," Spine (Phila Pa 1976), vol. 38, No. 21, Oct. 1, 2013, pp. 1832-1841.

Taiwanese Office Action and Search Report for Taiwanese Application No. 109142659, dated Nov. 11, 2021.

* cited by examiner

METHOD AND SYSTEM FOR 3D IMAGE DYNAMIC CORRECTION EVALUATION AND ORTHOTICS AUXILIARY DESIGN

This application claims the benefit of Taiwan application Serial No. 109142659, filed Dec. 3, 2020, the disclosure of which is incorporated by reference herein in its entirety.

TECHNICAL FIELD

The disclosure relates in general to a method and a system for 3D image dynamic correction evaluation and orthotics auxiliary design.

BACKGROUND

At present, production of scoliosis orthotics still generally uses the traditional plaster mold-taking method. However, the winding and tightness of the bandage are not the same, which can easily cause errors in taking the mold. Moreover, it takes a long time to take the mold. It is also difficult for the patient to maintain a fixed posture, and it is easy to cause errors in the mold taking. Therefore, plaster mold taking is time-consuming and laborious, and it is difficult to ensure the correct front-to-back symmetry of the torso. Orthotics scoliosis is therefore unable to obtain the correct production basis. The correction and comfort of the patient are also affected, and further improvement is needed.

SUMMARY

According to one embodiment, a method for 3D image dynamic correction evaluation and orthotics auxiliary design is provided. The method includes the following steps. A 3D scanning information of a human body is obtained. A plurality of 2D images is identified for calculating a plurality of pixel values of the 2D images and generating an original 3D spine curve. The 2D images and the 3D scanning information are overlapped. A deformed body shape of the human body is obtained via an image deformation prediction body shape correction method. A force position, a force direction and a force magnitude of an orthotics are predicted according to deformed body shape via a spine material property and mechanical model prediction method.

According to another embodiment, a system for 3D image dynamic correction evaluation and orthotics auxiliary design. The system includes a 3D scanning device, a processing unit, an image deformation prediction body shape correction unit, and a spine material property and mechanical model prediction unit. The 3D scanning device is configured to obtain a 3D scanning information of a human body. The processing unit is configured to identify a plurality of 2D images for calculating a plurality of pixel values of the 2D images and generating an original 3D spine curve. The processing unit overlaps the 2D images and the 3D scanning information. The image deformation prediction body shape correction unit is configured to obtain a deformed body shape of the human body. The spine material property and mechanical model prediction unit is configured to predict a force position, a force direction and a force magnitude of an orthotics according to the deformed body shape.

Figure 1A:
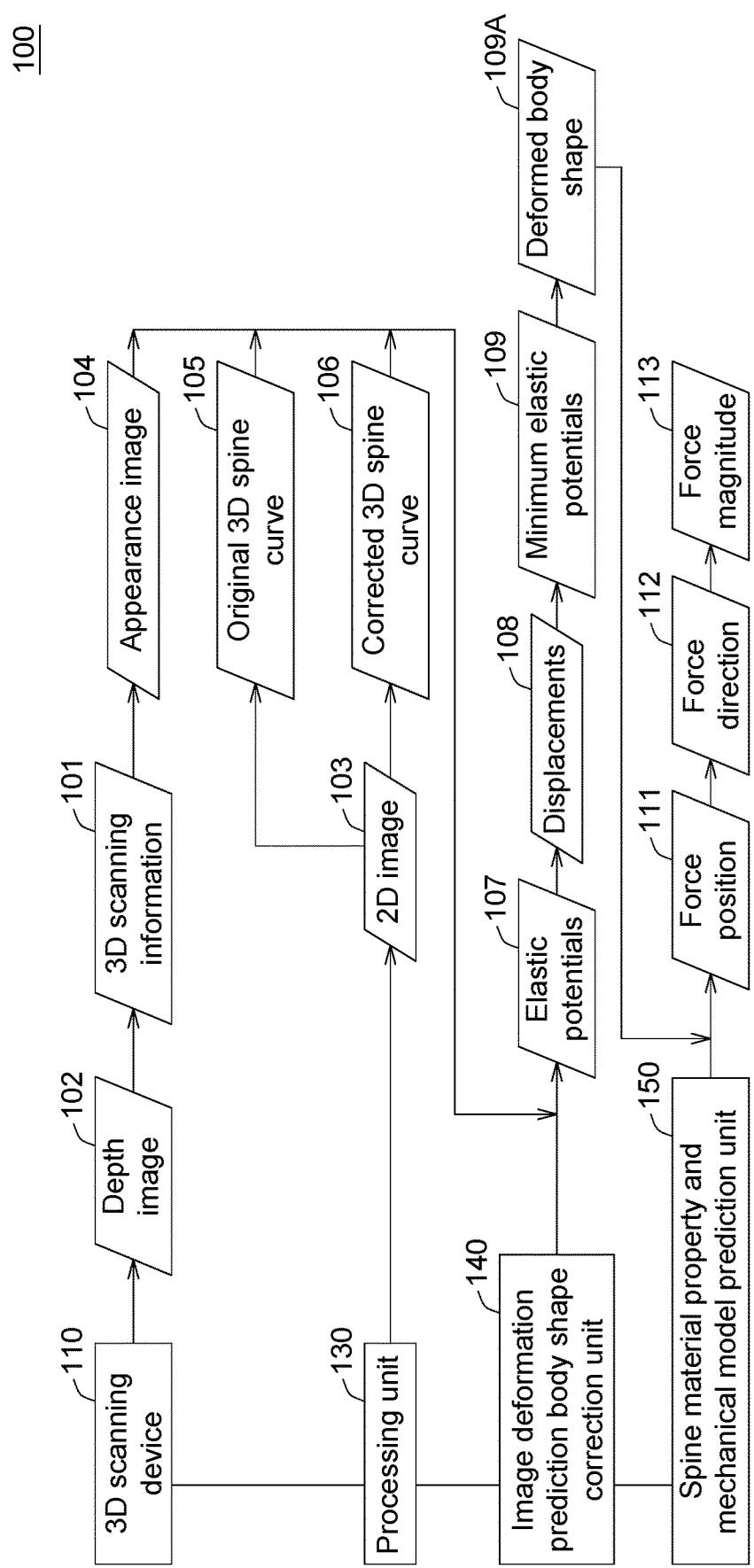
FIG. 1A illustrates a schematic diagram of a system for 3D image dynamic correction evaluation and orthotics auxiliary design according to an embodiment of the present invention.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

DETAILED DESCRIPTION

The following is a detailed description of the present embodiments, the embodiments are only used as an example to illustrate, not to limit the scope of the present invention to be protected. The following uses the same/similar symbols to indicate the same/similar components for explanation.

Figure 1B:
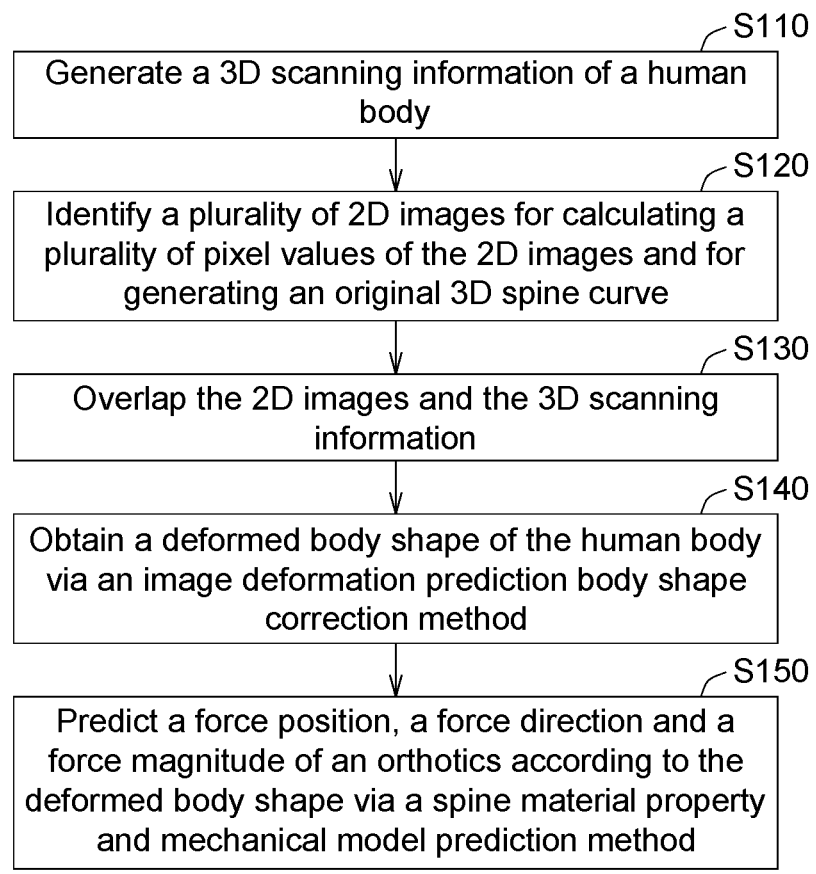
FIG. 1B shows a flowchart of a method for the 3D image dynamic correction evaluation and the orthotics auxiliary design according to an embodiment of the present invention.

Please refer to FIGS. 1A and 1B. FIG. 1A illustrates a schematic diagram of a system 100 for 3D image dynamic correction evaluation and orthotics auxiliary design according to an embodiment of the present invention. FIG. 1B shows a flowchart of a method for the 3D image dynamic correction evaluation and the orthotics auxiliary design according to an embodiment of the present invention.

According to one embodiment of the present invention, the system 100 includes a 3D scanning device 110, a processing unit 130, an image deformation prediction body shape correction unit 140 and a spine material property and mechanical model prediction unit 150.

The 3D scanning device 110 is used to generate a plurality of depth images 102. The 3D scanning device 110 generates a 3D scanning information 101 of a human body by modeling the depth images 102, and then constructs an appearance image 104 of the human body. As shown in FIG. 1B, in step S110, the 3D scanning information 101 of the human body is generated by modeling the depth images 102. The 3D scanning device 110 includes, for example, multiple depth cameras or LiDAR modules. The 3D scanning device 110 not only sets up a scanning space that completely covers the torso of the body to be scanned through mechanical design and opto-electromechanical integration, so as to scan the shape of the human body, it is also equipped with computing and modeling software. The computing and modeling software could calculate the depth information by modeling the depth image 102 obtained by scanning, so that the 3D scanning device 110 could create a 3D model of the human body in a short time.

The processing unit 130 obtains a plurality of 2D images 103 which are X-ray films for generating an original 3D spine curve 105 and a corrected 3D spine curve 106. The original 3D spine curve 105 is, for example, an image generated by superimposing the X-ray films taken by the patient, and the corrected 3D spine curve 106 is, for example, an image generated by a possible correction curve estimated through the X-ray films taken by the patient. That is to say, the processing unit 130 processes the 2D images 103 which are X-ray films. For example, the processing unit 130 uses Text detection to realize the automatic correction of the ruler number and ruler tilt of the X-ray films, and uses the Optical Character Recognition (OCR) technology to automatically recognize the ruler number in the 2D images 103 and calculate the actual pixel value. As shown in FIG. 1B, in step S120, the 2D images 103 are identified for calculating a plurality of pixel values of the 2D images 103 and for generating the original 3D spine curve 105.

The original 3D spine curve 105 could be compared with the data in the database to identify the type of spine in the original 3D spine curve 105. If it is identified that the type of spine needs to be corrected, what kind of curvature of the spine is determined for deciding a correction plan and the corrected 3D spine curve 106 is generated. The original 3D spine curve 105 and the corrected 3D spine curve 106 are overlapped with the appearance image 104 of the human body scanned by the 3D scanning device 110. As shown in FIG. 1B, in step S130, the 2D images 103 and the 3D scanning information 101 are overlapped.

In addition, the image deformation prediction body shape correction unit 140 is used to generate a deformed body shape 109A of the human body. If the processing unit 130 determines that the original 3D spine curve 105 is the type of spine that needs to be corrected, the image deformation prediction body shape correction unit 140 could deform the three-dimensional spine curve and the body shape, and display the change process of the original 3D spine curve 105, the corrected 3D spine curve 106 and the appearance image 104 of the human body. The deformation model could be corrected by the accumulation of big data. As shown in FIG. 1B, in step S140, the deformed body shape of the human body is obtained via an image deformation prediction body shape correction method.

In addition, the spine material property mechanical model prediction unit 150 is used to predict a force position 111, a force direction 112, and a force magnitude 113 of an orthotics 115 on the human body. After the analyst obtains the deformation model of the spine of the human body that needs to be corrected, the spine material property mechanical model prediction unit 150 could evaluate the most appropriate parameter values of the force position 111, the force direction 112, and the force magnitude 113 based on the biomechanical model and the results of the front and back body changes. As shown in FIG. 1B, in step S150, the force position 111, the force direction 112 and the force magnitude 113 of the orthotics are predicted according to the deformed body shape 109A via a spine material property and mechanical model prediction method.

Figure 2:
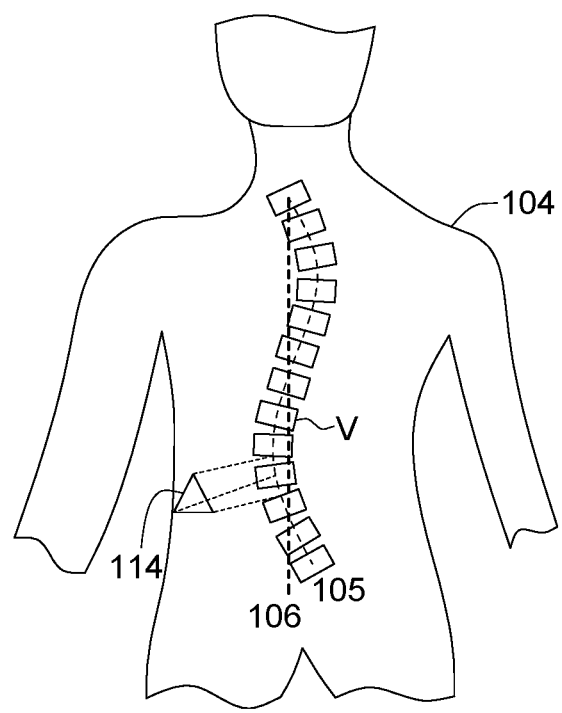
FIG. 2 shows a schematic diagram of overlapping the original 3D spine curve and the corrected 3D spine curve with the appearance image of the human body according to an embodiment of the present invention.
Figure 3:
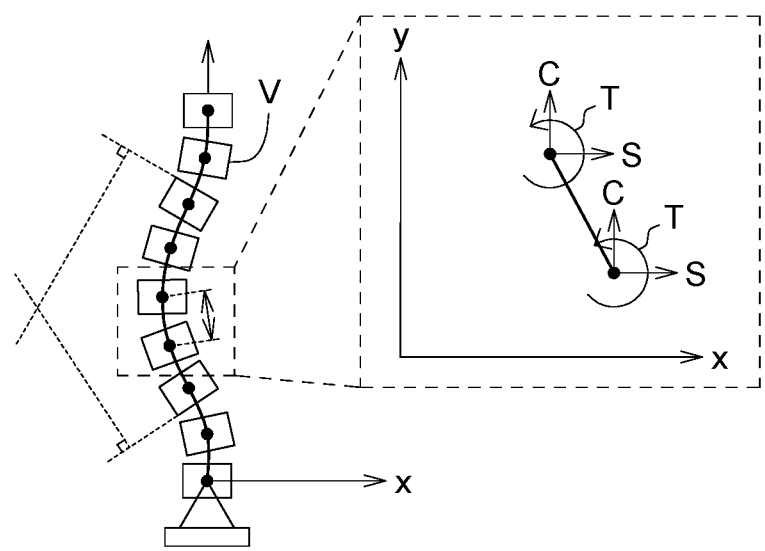
FIG. 3 shows a schematic diagram of identifying the 3D spine curve type of the human body.

Please refer to FIGS. 2 and 3. FIG. 2 shows a schematic diagram of overlapping the original 3D spine curve 105 and the corrected 3D spine curve 106 with the appearance image 104 of the human body according to an embodiment of the present invention. FIG. 3 shows a schematic diagram of identifying the 3D spine curve type of the human body. The system 100 and method for the 3D image dynamic correction evaluation and the orthotics auxiliary design could help orthopedics and rehabilitation physicians to predict the post-correction body shape and perform dynamic correction planning evaluation. In an embodiment, the dynamic correction plan may include an estimated correction period and a dynamic auxiliary correction design. The evaluation of the correction progress and expected effect could help orthopedics and rehabilitation physicians to determine the patient's required correction period. In addition, the dynamic correction design could calculate the deformed body shape 109A and the force position 111, the force direction 112 and the force magnitude 113 of the orthotics 115 on the human body at each stage based on the 3D body shape deformation model before and after the correction. The deviation models of the sagittal plane S with 75 deviation modes, the coronal plane C and the vertebral rotation T could be analyzed to estimate the required correction range and correction strength of each vertebra.

Figure 4:
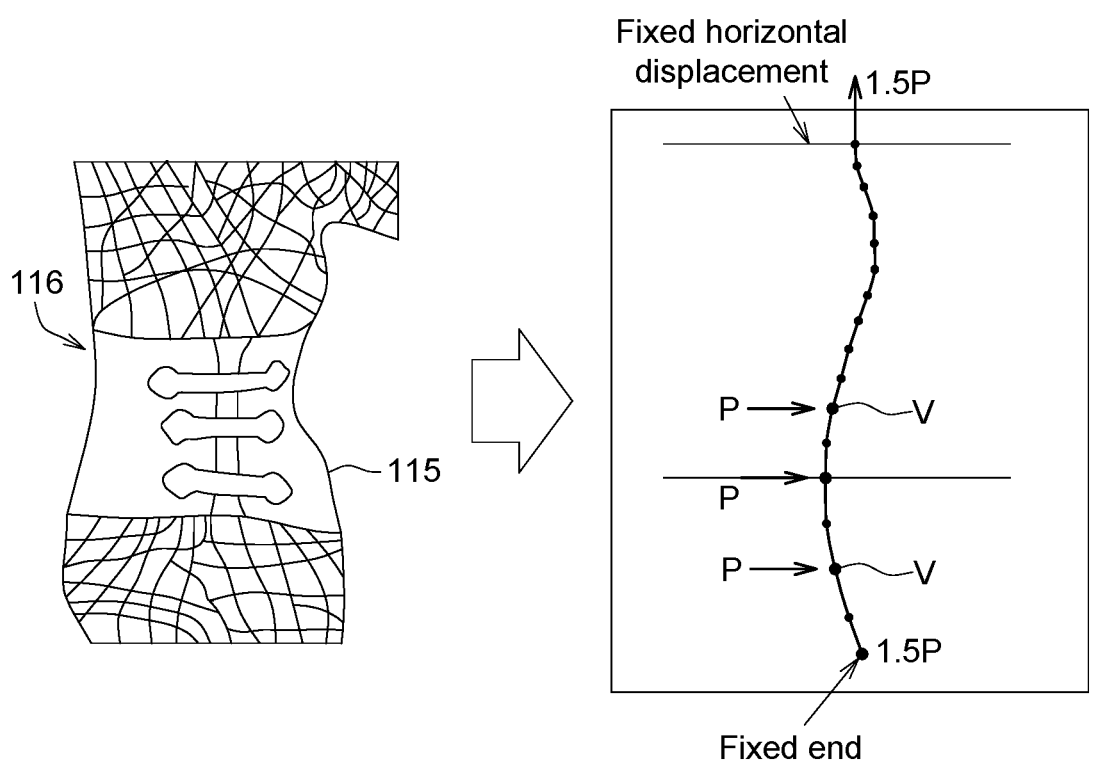
FIG. 4 which illustrates the force position, the force direction and the force magnitude of the orthotics on the human body.

Please refer to FIG. 4 which illustrates the force position 111, the force direction 112 and the force magnitude 113 of the orthotics 115 on the human body. In the subsequent orthotics auxiliary design, the finite element method could be used to analyze the biomechanical model of the human body spine, which will provide greater help for three-dimensional scoliosis correction and orthotics design. In the subsequent orthotics auxiliary design, the finite element method could be used to analyze the biomechanical model of the human body spine, which will provide greater help for 3D scoliosis correction and orthotics design. The optimal quantitative information of orthotics design for scoliosis, such as the pressure P applied to orthotics 115 for meeting the predetermined bending angle reduction, the force direction, the predetermined size of the pad, and the stress distribution of the vertebras, could be evaluated by the biomechanical model. The correction plan could be obtained by the intelligent 3D image dynamic correction. After numerical calculation, the scoliosis angle force magnitude, the stress on the intervertebral disc, the stress on the sacral could be obtained. The information are provided for physicians and orthotics design engineers to perform comprehensive evaluations on the numerical analysis results to determine the best three-dimensional scoliosis correction angle for individual patients and the design of scoliosis parameters to achieve the correction plan.

Please refer to FIG. 4, a finite element model 116 is established on the basis of a specific patient's scoliosis, and the patient's Computer Tomography (CT) medical image is used as the data for geometric construction in the process. The patient's spine geometry is converted to the finite element model 116 for relevant biomechanical analysis, but if high-quality 3D hexahedral elements are used in the biomechanical model, the calculation efficiency will be seriously affected. In order to solve these problems, this embodiment uses the X-ray films (2D images) with the human body's coronal plane and sagittal plane to descend the high-quality 3D model into two 2D equivalent finite element mode with the coronal plane C and sagittal plane S.

In this embodiment, this model is used to analyze the force condition of the scoliosis correction process, and the analysis result is fed back to the orthotics design. The purpose is to simulate and iteratively improve the orthotics design of scoliosis. The force position 111, the force magnitude 113, the force direction 112 and the stress on each vertebra V required to correct the deformation could be calculated on the coronal plane C and the sagittal plane S for the orthotics design.

Figure 5A:
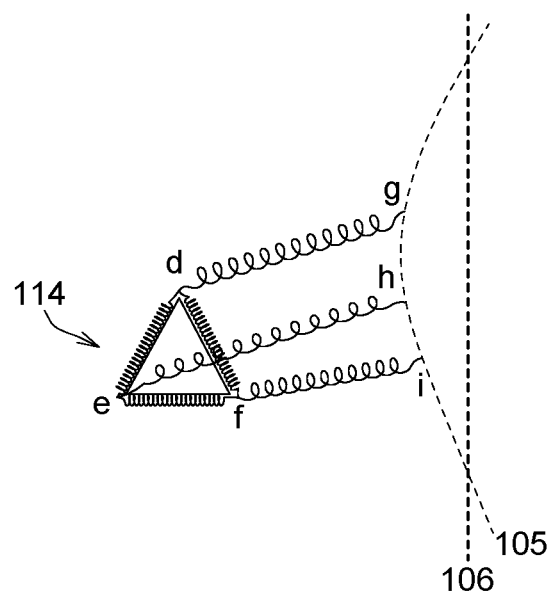
FIGS. 5A to 5D illustrate that elastic potentials, displacements, minimum elastic potentials of the nodes on the triangular mesh and the deformed body shape are obtained via the image deformation prediction body shape correction method.
Figure 5B:
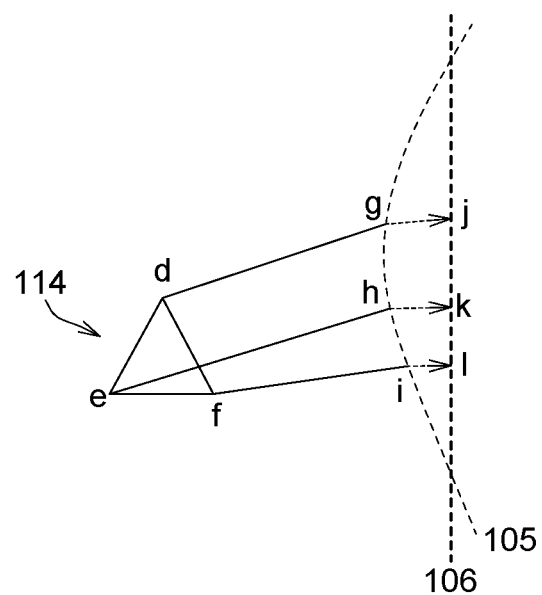
Figure 5C:
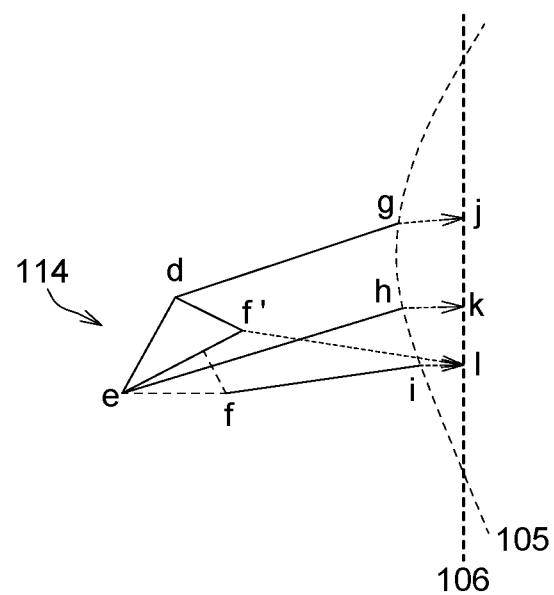
Figure 5D:
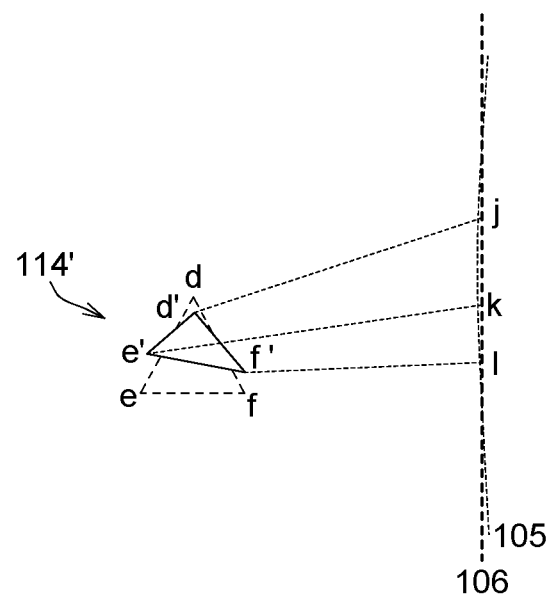
Figure 6:
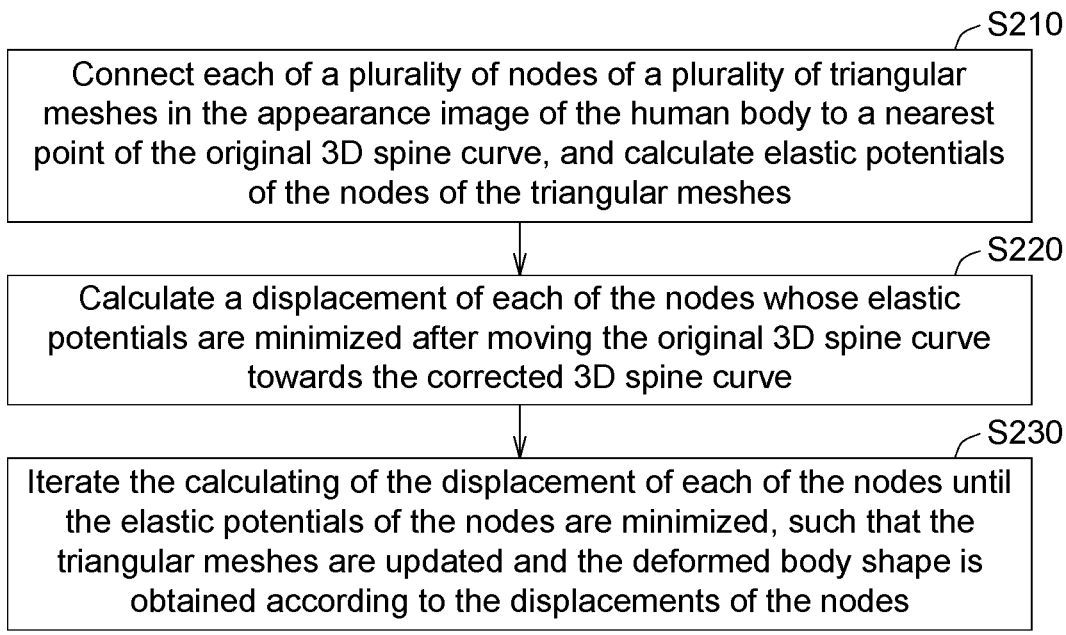
FIG. 6 shows a schematic diagram of steps respectively performed by parts of the image deformation prediction body shape correction unit according to an embodiment of the present invention.

Please refer to FIGS. 5A to 5D and FIG. 6. FIGS. 5A to 5D illustrate that elastic potentials 107, a displacement 108, minimum elastic potentials 109 of the nodes on the triangular mesh and the deformed body shape 109A are obtained via the image deformation prediction body shape correction method. FIG. 6 shows a schematic diagram of steps respectively performed by parts of the image deformation prediction body shape correction unit 140 according to an embodiment of the present invention.

Please refer to FIG. 5A, each node (d, e, f) of each triangular mesh 114 of the body shape is connected to the nearest point (g, h, i) on the original 3D spine curve 105. Each line (f-e, f-d, f-i) is assumed to be connected by a spring and obeys Hooke's law (F(x)=kx), where k is the elastic coefficient and x is the displacement 108. As shown in FIG. 6, taking the hardware part and/or software part of the image deformation prediction body shape correction unit 140 as an example, in step S210, each of a plurality of nodes of the triangular meshes 114 in the appearance image of the human body are connected to a nearest point of the original 3D spine curve, and elastic potentials 107 of the nodes of the triangular meshes are calculated.

Please refer to FIG. 5B, when the original 3D spine curve 105 is moved towards the corrected 3D spine curve 106 during the spine correction process, the point (g, h, i) moves towards the point (j, k, l). The elastic potentials of the nodes (d, e, f) of the triangular mesh 114 is calculated by $Ep(x)=\frac{1}{2}kx^2$. Please refer to FIG. 5C, when node i moves to node l, the three lines (f-e, f-d, f-i) will move to the three lines (f'-e, f'-d, f'-l) at which the elastic potentials of nodes of the triangular mesh 114 are minimized, and a displacement from the node f to the node f' is generated. As shown in FIG. 6, in step S220, a displacement 108 of each of the nodes whose elastic potentials are minimized after moving the original 3D spine curve 105 towards the corrected 3D spine curve 106 is calculated.

Please refer to FIG. 5D, the calculation of the elastic potentials 107 of nodes of the triangular mesh 114 is iterated according to the corresponding body shape, so that the elastic potentials reach are minimized. A new triangular mesh 114' (d', e', f') is obtained and a deformed body shape is generated based on the displacement 108 of each node. As shown in FIG. 6, in step S230, the calculating of the displacement 108 of each of the nodes is iterated until the elastic potentials 107 of the nodes are minimized, such that the triangular meshes 114 are updated and the deformed body shape 109A is obtained according to the displacements 108 of the nodes. In one embodiment, the cervical spine, thoracic spine and lumbar spine of the body will have different amounts of deformation given the same force, and the above-mentioned body shape parameter refers to the degree of difficulty (for example, Young's coefficient) of the body's mechanical model deformation.

As described above, the image deformation prediction body shape correction method in the above-mentioned FIGS. 5A to 5D and FIG. 6 could accurately predict the displacement 108 of the node of the human body, and generate a three-dimensional body shape deformation model before and after correction, such as the deformed body shape 109A. The above-mentioned correction is not limited to completing the correction of the spine curve at one time. The correction of the spine curve could also be completed in multiple stages according to the judgment of the doctor and the orthotics design engineer. In other words, the corrected 3D spine curve 106 could include several images of different stages.

Figure 7:
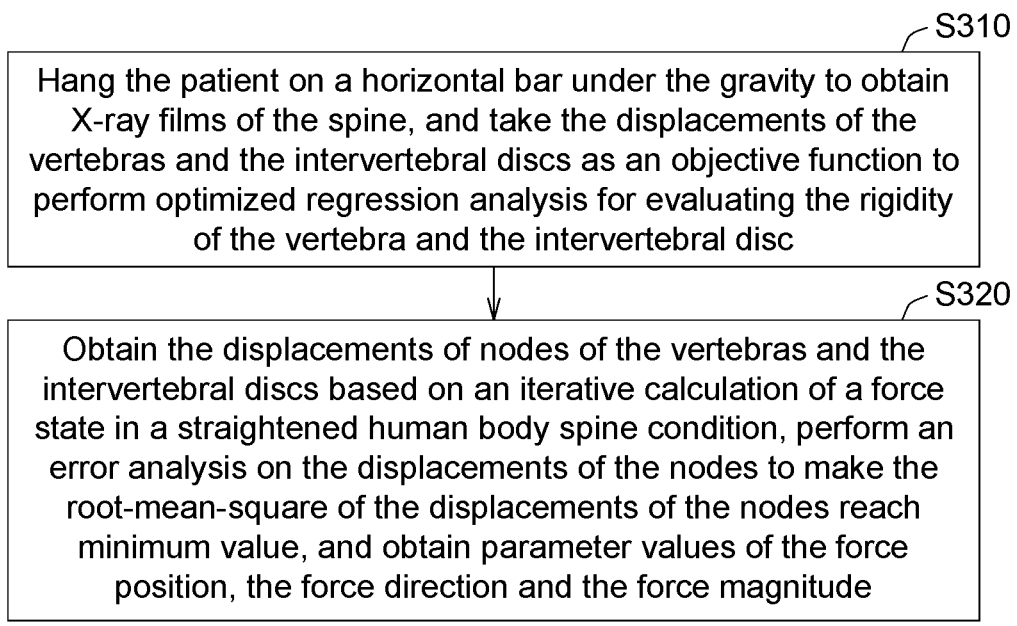
FIG. 7 is a schematic diagram of the steps respectively performed by parts of the spine material property and mechanical model prediction unit according to an embodiment of the present invention.
Figure 8:
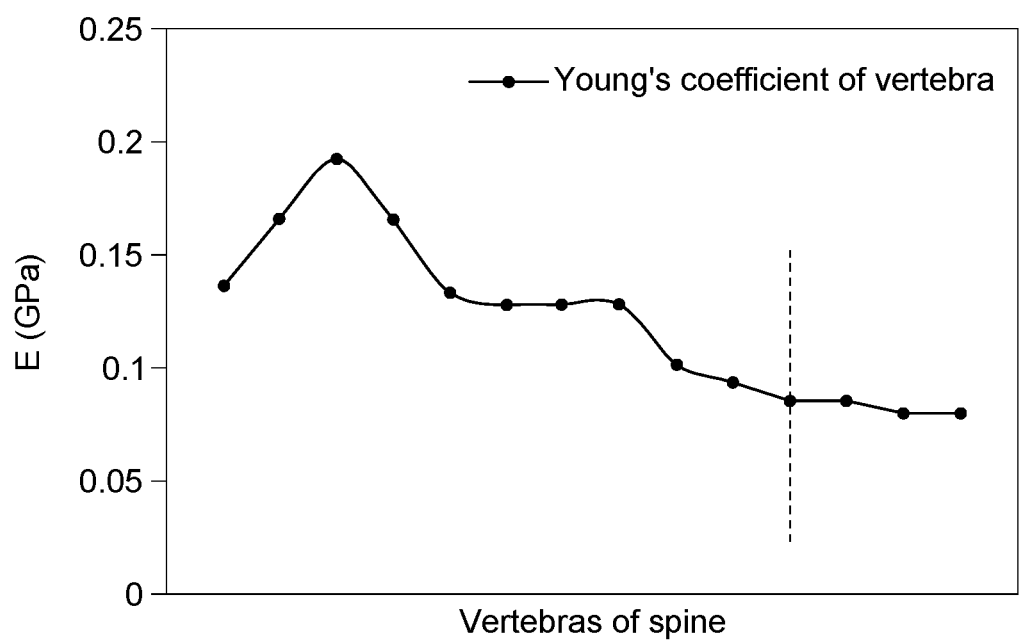
FIG. 8 shows a schematic diagram of the Young's modulus (E value) of each vertebra and intervertebral disc.

Please refer to FIGS. 7 and 8. FIG. 7 is a schematic diagram of the steps respectively performed by parts of the spine material property and mechanical model prediction unit 150 according to an embodiment of the present invention. FIG. 8 shows a schematic diagram of the Young's modulus (E value) of each vertebra and intervertebral disc.

The execution of spine material property and mechanical model prediction method is, for example, through biomechanical simulation with the iterating of the experimental regression analysis. In one embodiment, the experimental regression analysis is, for example, the patient are hanged on a horizontal bar under the gravity to obtain X-ray films of the spine, and the displacement ($\delta_i^*$) of the vertebra and the intervertebral disc is taking as an objective function. In the biomechanical model, modeling is carried out based on the state that the patient hangs on the horizontal bar under the gravity, and the relevant vertebra V and intervertebral disc geometry are used to perform optimized regression analysis to evaluate the rigidity of the vertebra V and the intervertebral disc. As shown in FIG. 7, taking the hardware part and/or software part of the spine material property and mechanical model prediction unit 150 as an example, in step S310, the patient are hanged on a horizontal bar under the gravity to obtain X-ray films of the spine, and the displacements of the vertebras and the intervertebral discs are taking as an objective function to perform optimized regression analysis for evaluating the rigidity of the vertebra V and the intervertebral disc.

The optimized regression analysis is as follows: A calculation of the movements ($\delta_i$) of the vertebras V and the intervertebral discs is iterated based on Young's modulus (E value). The error between the displacement ($\delta_i$) of each node and the displacements ($\delta_i^*$) of the objective function are calculated for performing an error analysis. A Young's modulus iterating convergence condition is that the root-mean-square of the movements of the vertebras and the intervertebral discs reaches a minimum value (about 0.1 to 0.3). The Young's modulus (E value) is shown in FIG. 8. As shown in FIG. 7, in step S320, the displacements of nodes of the vertebras V and the intervertebral discs are obtained based on an iterative calculation of a force state in a straightened human body spine condition, an error analysis is performed on the displacements of the nodes to make the root-mean-square of the displacements of the nodes reach minimum value, and parameter values of the force position 111, the force direction 112 and the force magnitude 113 are obtained.

Please refer to FIGS. 9A to 9F, which show schematic diagrams of the calculation of the elastic potentials 107, the displacement 108, the minimum elastic potentials 109 and the deformed body shape 109A via the image deformation prediction body shape correction method.

Figure 9A:
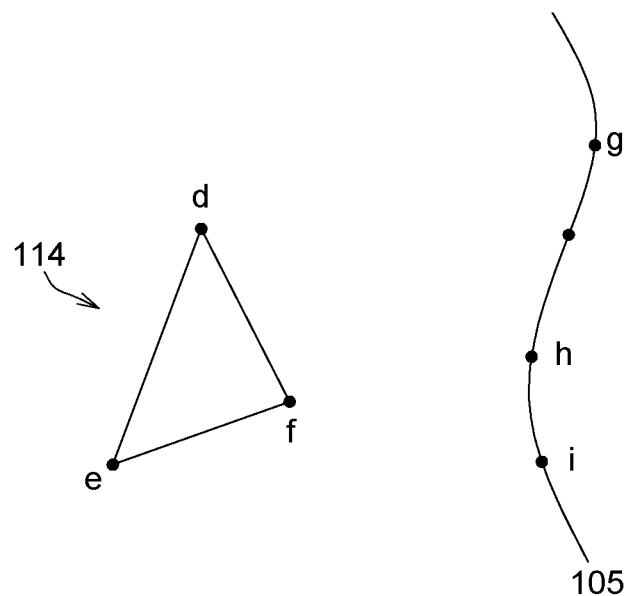
FIGS. 9A to 9F, which show schematic diagrams of the calculation of the elastic potentials, the displacements, the minimum elastic potentials and the deformed body shape via the image deformation prediction body shape correction method.
Figure 9B:
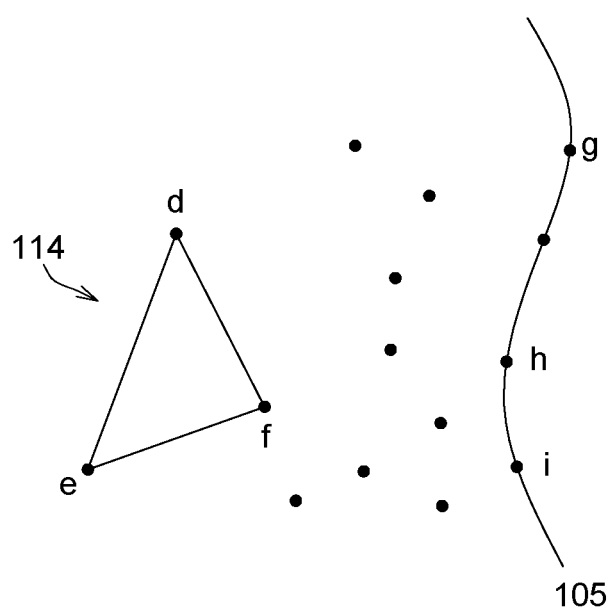
Figure 9C:
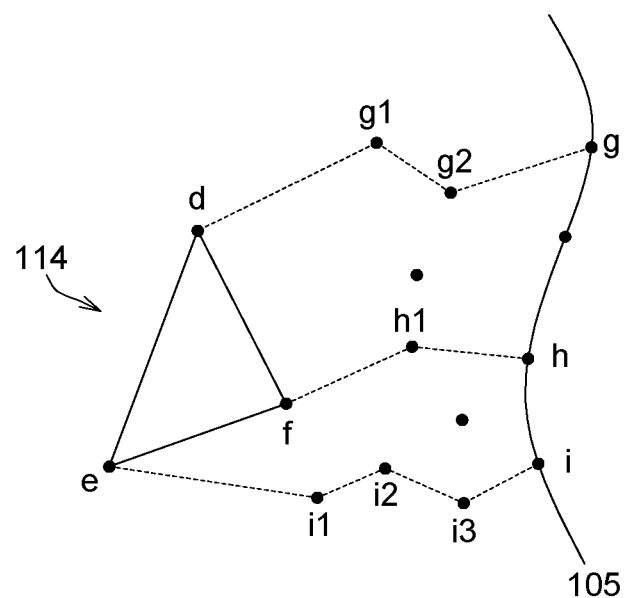
Figure 9D:
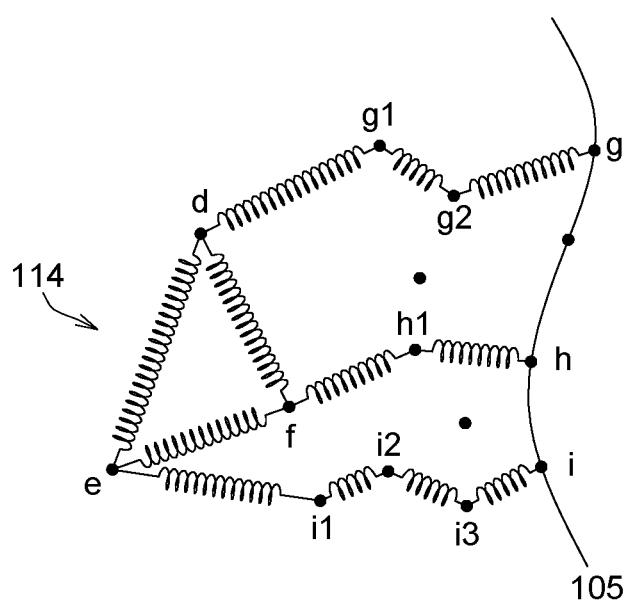
Figure 9E:
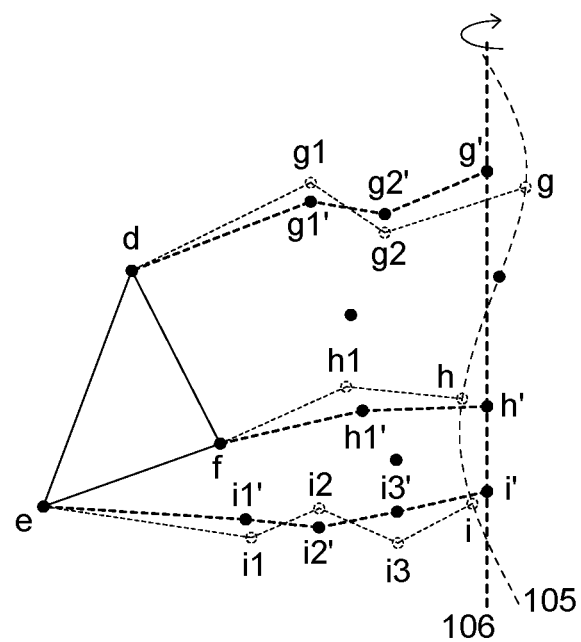
Figure 9F:
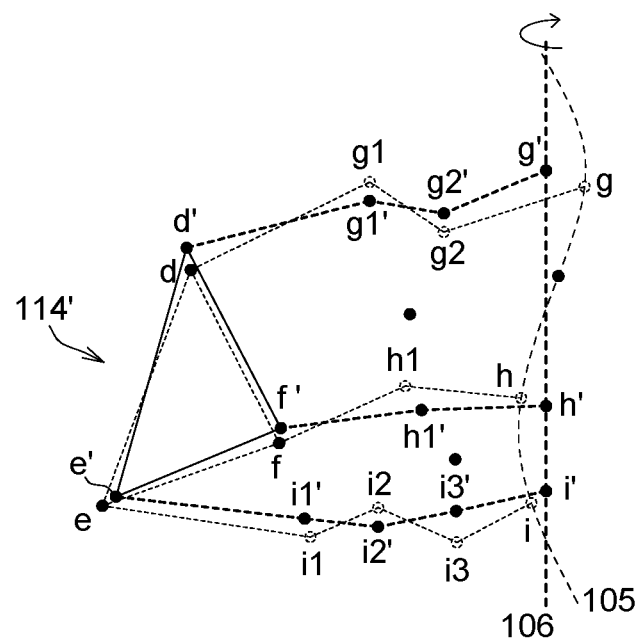

Please refer to FIG. 9A. Points corresponding to the intermediate point density are generated on the original 3D spine curve 105 according to Young's coefficient. In addition, please refer to FIG. 9B, a number of intermediate points are generated inside the body according to the point cloud density. The intermediate points could be generated, for example, according to the structure of the human body or evenly generated. Please refer to FIG. 9C, each node (d, e, f) of each triangular mesh 114 of the body shape is connected to the nearest intermediate point (g1, h1, i1), and look for possible intermediate points. For example, the intermediate point (g1) is connected to the nearest point (g) on the original 3D spine curve 105 through the intermediate point (g2), and the intermediate point (i1) is connected to the nearest point (i) on the original 3D spine curve 105 through the intermediate point (i2, i3). Please refer to FIG. 9D. It is assumed that each connected line is pulled by a spring and obeys Hooke's law (F(x)=kx), the current length is the lowest energy state. Please refer to FIG. 9E, when the spine is adjusted or rotated according to the user's needs during the spine correction, the body shape is approached from the original 3D spine curve 105 to the corrected 3D spine curve 106, and the node (g, h, i) approaches the node (g', h', I'), make each intermediate point (g1, g2, h1, i1, i2, i3) move to the new intermediate point (g1', g2', i1', i2', i3'). The elastic potentials 107 of the endpoint of the triangular mesh 114 and the intermediate point is calculated to make the elastic potentials 107 reach the minimum elastic potentials 109 to generate the displacement 108 and the amount of rotation of these nodes. Please refer to FIGS. 9E and 9F. According to the body shape parameters, the elastic potentials 107 of the endpoints and the intermediate points of the triangular mesh 114 are iteratively calculated to make the elastic potentials being minimized, and obtain the new triangular mesh 114' (d', e', f') to produce the deformed body shape 109A.

As described above, the image deformation prediction body shape correction methods in FIGS. 9A to 9D could accurately predict the displacement 108 and the amount of rotation of the respective endpoints of the human body, thereby generating a three-dimensional body shape deformation model.

The method for the 3D image dynamic correction evaluation and the orthotics auxiliary design of the above embodiment of the present invention could obtain the 3D scanning information through 3D scanning, and synthesize the 2D image and the 3D scanning information of the human body, thereby identifying the 3D image of the human body spine curve type. In addition to providing designers with accurate corrected 3D spine curve, it could also accumulate big data to provide analysts with the required 3D image dynamic correction evaluation and the orthotics auxiliary design, which overcomes the shortcomings of traditional plaster model-taking methods for making the orthotics and improves the comfort and treatment effect of patients during treatment.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A method for 3D image dynamic correction evaluation and orthotics auxiliary design, comprising:
   obtaining a 3D scanning information of a human body;
   identifying a plurality of 2D images for calculating a plurality of pixel values of the 2D images and generating an original 3D spine curve;
   overlapping the 2D images and the 3D scanning information;
   obtaining a deformed body shape of the human body via an image deformation prediction body shape correction method; and
   predicting a force position, a force direction and a force magnitude of an orthotics according to the deformed body shape via a spine material property and mechanical model prediction method.

2. The method for the 3D image dynamic correction evaluation and the orthotics auxiliary design according to claim 1, wherein the image deformation prediction body shape correction method comprises:
   overlapping the 2D images of the human body to generate the original 3D spine curve and a corrected 3D spine curve, and overlapping the original 3D spine curve and the corrected 3D spine curve with an appearance image of the human body;
   connecting each of a plurality of nodes of a plurality of triangular meshes in the appearance image of the human body to a nearest point of the original 3D spine curve, and calculating elastic potentials of the nodes of the triangular meshes;
   calculating a displacement of each of the nodes whose elastic potentials are minimized after moving the original 3D spine curve towards the corrected 3D spine curve; and
   iterating the calculating of the displacement of each of the nodes until the elastic potentials of the nodes are minimized, such that the triangular meshes are updated and the deformed body shape is obtained according to the displacements of the nodes.

3. The method for the 3D image dynamic correction evaluation and the orthotics auxiliary design according to claim 2, wherein the corrected 3D spine curve comprises a plurality of stages of corrected 3D spine curves.

4. The method for the 3D image dynamic correction evaluation and the orthotics auxiliary design according to claim 1, wherein the image deformation prediction body shape correction method comprises:
   overlapping the 2D images of the human body to generate the original 3D spine curve and a corrected 3D spine curve, and overlapping the original 3D spine curve and the corrected 3D spine curve with an appearance image of the human body;
   creating a plurality of intermediate points in the human body, connecting each of a plurality of nodes of a plurality of triangular meshes in the human body to one of the intermediate points which is nearest, and connecting each of the intermediate points to a nearest point of the original 3D spine curve;
   calculating elastic potentials of the nodes of the triangular meshes and the intermediate points;
   calculating a displacement and a rotation of each of the nodes and the intermediate points whose elastic potentials are minimized after moving the original 3D spine curve towards the corrected 3D spine curve; and
   iterating the calculating of the displacement of each of the nodes and the intermediate points until the elastic potentials of the nodes and the intermediate points are minimized, such that the triangular meshes are updated and the deformed body shape is obtained according to the displacements of the nodes and the intermediate points.

5. The method for the 3D image dynamic correction evaluation and the orthotics auxiliary design according to claim 1, wherein the spine material property and mechanical model prediction method comprises:
   obtaining the 2D images of the human body that are hanged on a horizontal bar under gravity, and performing an optimized regression analysis to evaluate rigidities of a plurality of vertebras and a plurality of intervertebral discs by taking movements of the vertebras and the intervertebral discs of the human body under the gravity as an objective function; and iterating, in a straightened human body spine condition, the optimized regression analysis and performing an error analysis on a plurality of displacements of a plurality of nodes and the displacements of the objective function until a root-mean-square of the movements of the vertebras and the intervertebral discs is minimized, such that the force position, the force direction and the force magnitude are obtained.

6. The method for the 3D image dynamic correction evaluation and the orthotics auxiliary design according to claim 5, wherein in the optimized regression analysis, a calculation of the movements of the vertebras and the intervertebral discs is iterated based on Young's modulus, and a Young's modulus iterating convergence condition is that the root-mean-square of the movements of the vertebras and the intervertebral discs reaches a minimum value.

7. The method for the 3D image dynamic correction evaluation and the orthotics auxiliary design according to claim 5, wherein in the spine material property and mechanical model prediction method, a biomechanical model of a spine of the human body is analyzed by a finite element method, and the biomechanical model which is a 3D model is descended to be a 2D equivalent finite element model with a coronal plane and a sagittal plane according to the 2D images with the coronal plane and the sagittal plane.

8. The method for the 3D image dynamic correction evaluation and the orthotics auxiliary design according to claim 1, wherein in the step of identifying the 2D images, a text detection or an optical character recognition is used for identifying the 2D images.

9. The method for the 3D image dynamic correction evaluation and the orthotics auxiliary design according to claim 1, wherein in the 3D image dynamic correction evaluation, the deformed body shape, the force position, the force direction, and the force magnitude at each stage are calculated according to a 3D body shape deformation model before and after correction.

10. The method for the 3D image dynamic correction evaluation and the orthotics auxiliary design according to claim 1, in the orthotics auxiliary design, a pressure applied by the orthotics is calculated to meet a predetermined bending angle reduction, the force direction, a predetermined size of a pad and a vertebra stress distribution according to a 3D body shape deformation model before and after correction.

11. A system for 3D image dynamic correction evaluation and orthotics auxiliary design, comprising:
   a 3D scanning device, configured to obtain a 3D scanning information of a human body;
   a processing unit, configured to identify a plurality of 2D images for calculating a plurality of pixel values of the 2D images and generating an original 3D spine curve, wherein the processing unit overlaps the 2D images and the 3D scanning information;
   an image deformation prediction body shape correction unit, configured to obtain a deformed body shape of the human body; and
   a spine material property and mechanical model prediction unit, configured to predict a force position, a force direction and a force magnitude of an orthotics according to the deformed body shape.

12. The system for the 3D image dynamic correction evaluation and the orthotics auxiliary design according to claim 11, wherein the image deformation prediction body shape correction unit comprises:
   a first part, configured to overlap the 2D images of the human body to generate the original 3D spine curve and a corrected 3D spine curve, and overlap the original 3D spine curve and the corrected 3D spine curve with an appearance image of the human body;
   a second part, configured to connect each of a plurality of nodes of a plurality of triangular meshes in the appearance image of the human body to a nearest point of the original 3D spine curve, calculate elastic potentials of the nodes of the triangular meshes, and calculate displacements of the nodes whose elastic potentials are minimized after moving the original 3D spine curve towards the corrected 3D spine curve; and
   a third part, configured to iterate the calculating of the displacement of each of the nodes until the elastic potentials of the nodes are minimized, such that the triangular meshes are updated and the deformed body shape is obtained according to the displacements of the nodes.

13. The system for the 3D image dynamic correction evaluation and the orthotics auxiliary design according to claim 11, wherein the image deformation prediction body shape correction unit comprises:
   a first part, configured to overlap the 2D images of the human body to generate the original 3D spine curve and a corrected 3D spine curve, and overlap the original 3D spine curve and the corrected 3D spine curve with an appearance image of the human body;
   a second part, configured to create a plurality of intermediate points in the human body, connect each of a plurality of nodes of a plurality of triangular meshes in the human body to one of the intermediate points which is nearest, and connect each of the intermediate points to a nearest point of the original 3D spine curve;
   a third part, configured to calculate elastic potentials of the nodes of the triangular meshes and the intermediate points, and calculate a displacement and a rotation of each of the nodes and the intermediate points whose elastic potentials are minimized after moving the original 3D spine curve towards the corrected 3D spine curve; and
   a fourth part, configured to iterate the calculating of the displacement of each of the nodes and the intermediate points until the elastic potentials of the nodes and the intermediate points are minimized, such that the triangular meshes are updated and the deformed body shape is obtained according to the displacements of the nodes and the intermediate points.

14. The system for the 3D image dynamic correction evaluation and the orthotics auxiliary design according to claim 11, wherein the spine material property and mechanical model prediction unit comprises:
   a first part, configured to obtain the 2D images of the human body that are hanged on a horizontal bar under gravity, and perform an optimized regression analysis to evaluate rigidities of a plurality of vertebras and a plurality of intervertebral discs by taking movements of the vertebras and the intervertebral discs of the human body under the gravity as an objective function; and
   a second part, configured to iterate the optimized regression analysis in a straightened human body spine condition, and perform an error analysis on a plurality of displacements of a plurality of nodes and the displacements of the objective function, until a root-mean-square of the movements of the vertebras and the intervertebral discs is minimized, such that the force position, the force direction and the force magnitude are obtained.

15. The system for the 3D image dynamic correction evaluation and the orthotics auxiliary design according to claim 14, wherein in the optimized regression analysis, a calculation of the movements of the vertebras and the intervertebral discs is iterated based on Young's modulus, and a Young's modulus iterating convergence condition is that the root-mean-square of the movements of the vertebras and the intervertebral discs reaches a minimum value.

16. The system for the 3D image dynamic correction evaluation and the orthotics auxiliary design according to claim 14, wherein the spine material property and mechanical model prediction unit analyzes a biomechanical model of a spine of the human body by a finite element method, and descends the biomechanical model which is a 3D model to be a 2D equivalent finite element model with a coronal plane and a sagittal plane according to the 2D images with the coronal plane and the sagittal plane.

* * * * *